United States Patent [19]
Schlegel

[11] Patent Number: 5,364,937
[45] Date of Patent: Nov. 15, 1994

[54] PROCESSES FOR PREPARING SULFONYLUREAS

[75] Inventor: Günter Schlegel, Liederbach, Germany

[73] Assignee: Hoechst Aktiengesellschaft, Frankfurt am Main, Germany

[21] Appl. No.: 26,557

[22] Filed: Mar. 4, 1993

[30] Foreign Application Priority Data

Mar. 7, 1992 [DE] Germany .................... 4207242

[51] Int. Cl.$^5$ .................. C07D 239/42; C07D 239/47; C07D 251/46; C07D 251/52
[52] U.S. Cl. .................... 544/194; 544/211; 544/210; 544/205; 544/206; 544/208; 544/213; 544/196; 544/197; 544/199; 544/320; 544/321; 544/323; 544/332
[58] Field of Search ............... 544/194, 321, 211, 210, 544/205, 206, 208, 213, 196, 197, 199, 320, 323, 332

[56] References Cited

U.S. PATENT DOCUMENTS

| | | | |
|---|---|---|---|
| 3,931,277 | 1/1976 | Lohaus | 260/545 K |
| 4,191,553 | 4/1980 | Reap | 544/211 |
| 4,601,747 | 7/1986 | Willms et al. | 544/194 |
| 5,104,443 | 4/1992 | Kehne et al. | 544/321 |

FOREIGN PATENT DOCUMENTS

| | | |
|---|---|---|
| 0004163 | 9/1979 | European Pat. Off. |
| 0013258 | 7/1980 | European Pat. Off. |
| 0342569 | 11/1989 | European Pat. Off. |
| 2257240 | 5/1974 | Germany |

Primary Examiner—John M. Ford
Attorney, Agent, or Firm—Curtis, Morris & Safford

[57] ABSTRACT

Compounds of the formula I or salts thereof, $$R^1-X-\underset{\underset{O}{\overset{\overset{O}{\|}}{S}}}{\overset{\|}{\underset{R^6}{|}}}-N-\overset{O}{\overset{\|}{C}}-\underset{R^5}{\overset{|}{N}}\diagup\hspace{-1em}\begin{array}{c}N=\!\!\!\!\diagdown R^3\\ \\Y\\ \\N=\!\!\!\!\diagdown R^4\end{array}$$

in which
X is oxygen, —O—NR$^2$— or —SO$_2$—NR$^2$—, and Y is N or CH,
R$^1$ is (C$_1$-C$_6$)alkyl, (C$_2$-C$_6$)alkenyl or (C$_2$-C$_6$)alkynyl, which are in each case optionally substituted, or, in the case where X=oxygen, also (subst.) phenyl,
R$^2$ is H, (C$_1$-C$_6$)alkyl, (C$_2$-C$_6$)alkenyl or -alkynyl or (C$_3$-C$_6$) cycloalkyl,
R$^3$ and R$^4$ are H, (subst.) (C$_1$-C$_4$)alkyl or (subst.) (C$_1$-C$_4$)alkoxy or halogen, (C$_1$-C$_4$)alkylthio, (C$_1$-C$_4$)alkylamino or di[(C$_1$-C$_4$)alkyl]-amino,
R$^5$ is H or (C$_1$-C$_4$)alkyl and R$^6$ is hydrogen, may be prepared by reacting compounds of the formula II, $$R^1-X-R^7 \qquad (II)$$

with compounds of the formulae III, IV and V $$R^8-OCN \qquad (III)$$

$$SO_2Cl_2 \qquad (IV)$$

$$HN\diagup\hspace{-1em}\begin{array}{c}N=\!\!\!\!\diagdown R^3\\ \\Y\\ \\N=\!\!\!\!\diagdown R^4\end{array}\overset{|}{R^5} \qquad (V)$$

where R$^7$ and R$^8$ are H, a quarternary ammonium ion or one equivalent of a metal cation. The structure of the intermediate compounds has not been determined.

12 Claims, No Drawings

PROCESSES FOR PREPARING SULFONYLUREAS

The invention relates to processes for preparing heterocyclically substituted sulfonylurea herbicides, especially compounds of the formula I,

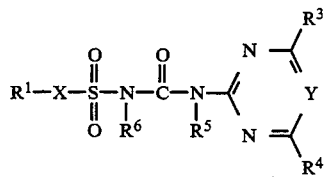

in which
X is oxygen, $-O-NR^2-$ or $-SO_2-NR^2-$,
Y is nitrogen or CH,
$R^1$ is $(C_1-C_6)$alkyl, $(C_2-C_6)$alkenyl or $(C_2-C_6)$alkynyl, where each of the latter three radicals, independently of each other, is unsubstituted or substituted by one or more radicals selected from the group comprising halogen, $(C_1-C_4)$alkoxy and $[(C_1-C_4)$alkoxy]-carbonyl, or, in the case where X=oxygen, also phenyl, which is unsubstituted or substituted by one or more radicals selected from the group comprising halogen, nitro, $(C_1-C_4)$alkyl, $(C_1-C_4)$haloalkyl, $(C_1-C_4)$alkoxy, $(C_1-C_4)$haloalkoxy and $[(C_1-C_4)$alkoxy]-carbonyl,
$R^2$ is hydrogen, $(C_1-C_6)$alkyl, $(C_2-C_6)$alkenyl, $(C_2-C_6)$alkynyl or $(C_3-C_6)$cycloalkyl,
$R^3$ and $R^4$ independently of each other, are hydrogen, $(C_1-C_4)$alkyl or $(C_1-C_4)$alkoxy, where each of the latter two radicals is unsubstituted or substituted by one or more radicals selected from the group comprising halogen, alkoxy and alkylthio, or is halogen, $(C_1-C_4)$alkylthio, $(C_1-C_4)$alkylamino or di[($C_1-C_4)$alkyl]-amino and
$R^5$ is hydrogen or $(C_1-C_4)$alkyl and
$R^6$ is hydrogen,
and salts thereof with acids or bases.

Formula I also comprises all the unspecified possible stereoisomers which are definable by their specific shape in space, such as enantiomers, diastereomers and Z and E isomers, which possess the combination of atoms given in formula I. Such compounds of the formula I contain, for example, one or more asymmetric carbon atoms or double bonds which are not especially indicated in the formula I. The stereoisomers may be obtained by customary methods from mixtures of the stereoisomers or be prepared by stereoselective reactions in combination with the use of stereochemically pure starting materials.

The compounds of the formula I can form salts in which the hydrogen of the $-SO_2-NH-$ group is replaced by a cation which is suitable, in particular, for agriculture. These salts are, for example, metal salts, in particular alkali metal salts (e.g. with $Na^+$ or $K^+$ as the cation) or alkaline earth metal salts, or ammonium salts or salts with organic amines. Salt formation can also take place by the addition of a strong acid to the pyrimidine moiety of the compound of the formula I. Suitable acids for this purpose are strong inorganic and organic acids, for example HCl, HBr, $H_2SO_4$ or $HNO_3$.

Compounds of the formula I are known and are employed as plant protective agents with herbicidal activity; see EP-A-013258 (US-A-4,601,747), EP-A-0342569 (US-A-5,104,443) and EP-A-4163 (US-A-4,191,553). In these said documents some processes according to which compounds of the formula I can be prepared are also cited or described.

A disadvantage of the known processes is the use of chlorosulfonyl isocyanate (CSI), whose high reactivity gives rise to safety problems and whose difficult obtainability leads to high costs. The known processes are therefore unfavorable for implementation on the industrial scale, from the point of view of both safety and expense.

A novel process has now been found according to which compounds of the formula I can be prepared in a surprisingly efficient manner by the reaction of readily available starting materials.

The present invention relates to a process for preparing the said compounds of the formula I, or their salts, wherein compounds of the formula II, $$R^1-X-R^7 \qquad (II)$$

in which $R^1$ and X are defined as in formula I and $R^7$ is hydrogen, a quaternary ammonium ion or one equivalent of a singly, doubly or multiply charged metal cation, are reacted with compounds of the formulae III, IV and V, $$R^8-OCN \qquad (III)$$

$$SO_2Cl_2 \qquad (IV)$$

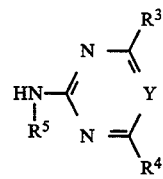

in which $R^3$, $R^4$, $R^5$, X and Y are defined as in formula I and $R^8$ is hydrogen, a quaternary ammonium ion or one equivalent of a singly, doubly or multiply charged metal cation.

Those processes according to the invention for preparing compounds of the formula I are of particular interest in which $R^1-X$ is $N[(C_1-C_6)$-alkylsulfonyl]-N-$[(C_1-C_3)$alkyl]-amino or $[(C_1-C_4)$alkoxy]-phenoxy, $R^3$ and $R^4$, independently of each other, are $(C_1-C_2)$alkyl or $(C_1-C_2)$alkoxy and $R^5$ is hhydrogen or methyl and $R^6$ is hydrogen.

$R^1-X$ is preferably N-$[(C_1-C_3)$-alkylsulfonyl]-N-$[(C_1-C_2)$alkyl]-amino, in particular N-(methylsulfonyl)-N-(methyl)-amino, N-(methylsulfonyl)-N-(ethyl)-amino, N-(ethylsulfonyl)-N-(methyl)-amino or N-(n-propylsulfonyl)-N-(methyl)-amino; $R^1-X$ is also preferably $(C_1-C_3)$-alkoxyphenoxy, in particular 2-methoxyphenoxy, 2-ethoxyphenoxy, 2-n-propoxy-phenoxy or 2-isopropoxyphenoxy.

$R^3$ and $R^4$ independently of each other, are preferably $(C_1-C_2)$alkyl or $(C_1-C_2)$alkoxy, in particular methyl or methoxy.

Examples of $R^7$ and $R^8$ are alkali metal cations or alkaline earth metal cations such as sodium ions, potassium ions, magnesium ions and calcium ions. In the case of metal cations with a charge of more than 1, two or more radicals of the formula $R^1-X$ in compounds of the formula II and several of the radicals OCN in compounds of the formula III are correspondingly bound to the metal ions. Examples of $R^7$ and $R^6$ are also quaternary ammonium ions such as tetraalkylammonium, trialkylarylammonium, dialkyldiarylammonium, alkyltriarylammonium and tetraarylammonium, where the alkyl radicals may, where appropriate, be substituted, e.g. by alkoxy or aryl.

In the said formulae and below, hydrocarbon-containing radicals such as for example, alkyl, alkoxy, haloalkoxy and alkylthio radicals, as well as the corresponding unsaturated and/or substituted radicals in the hydrocarbon moiety, can in each case be straight-chain or branched. Alkyl radicals, in the composite senses such as alkoxy, haloalkyl etc., as well, are methyl, ethyl, n- or i-propyl, n-, i-, t- or 2-butyl; alkenyl and alkynyl radicals have the meaning of the possible unsaturated radicals corresponding to the alkyl radicals, such as 2-propenyl, 2- or 3-butenyl, 2-propynyl or 2- or 3-butynyl. Halogen is fluorine, chlorine, bromine or iodine. Haloalkyl is alkyl which is substituted by one or more atoms selected from the group comprising halogen; haloalkyl is, for example, $CF_3$, $CHF_2$ or $CH_2CF_3$. Aryl is, for example, phenyl, naphthyl, tetrahydronaphthyl, indanyl, fluorenyl and the like, preferably phenyl. Substituted aryl or substituted phenyl is preferably aryl or phenyl which is substituted by one or more, preferably 1 to 3, radicals selected from the group comprising halogen, alkyl, haloalkyl, haloalkoxy, nitro, cyano, alkoxycarbonyl, alkanoyl, carbamoyl, mono- and dialkylaminocarbonyl, mono- and di-alkylamino, alkylsulfinyl or alkylsulfonyl, where the preferred alkyl-containing radicals are those with 1 to 4 carbon atoms, in particular 1 to 2 carbon atoms; particularly preferred in this context are methyl, methoxy and chlorine.

The yields of the resulting sulfonylureas of the formula I, as prepared by the process according to the invention, are relatively high, e.g. 80% and more, with purities of more than 94% by weight being obtained, generally without elaborate purification steps.

The reaction is preferably carried out in two or more stages. In the first of these the compounds of the formulae II, III and IV are reacted with each other. Then compounds of the formula V are added to the reaction mixture obtained in this way. Intermediates arising in conjunction with the mixing of the reactants can be isolated as a rule. However, the whole process may also be carried out as a one-pot process.

The temperatures for the reactions of the components II, III and IV are preferably between 0° C. and +200° C., in particular between +80° C. and +135° C., very particularly between +20° C. and +90° C.

The temperature for the reaction of the reaction mixture consisting of II, III and IV with the aminoheterocycle V is preferably between −20° C. and +120° C., in particular between −5° C. and +80° C.

The process according to the invention may be carried out without solvents. However, it is often advantageous to carry out the process, or individual stages of the process, in the presence of inorganic or organic solvents which are inert under the reaction conditions, or in mixtures of these solvents. It can also be advantageous to change the solvent between the component stages of the process.

Suitable organic solvents are, for example, aprotic polar organic solvents, such as aliphatic or aromatic nitriles, N,N-dialkyl-alkanecarboxamides, dialkyl sulfoxides, polyalkylene glycol dialkyl ethers and N-alkylated cyclic amides, and aliphatic or, preferably, aromatic, where appropriate halogenated, hydrocarbons, or mixtures of the said organic solvents. Suitable inorganic solvents are, for example, liquid sulfur dioxide and liquid hydrocyanic acid, and their mixtures. Mixtures of the said organic and inorganic solvents are also possible.

Solvents which are preferred are those such as, for example, acetonitrile, propionitrile, benzonitrile, dimethylformamide, dimethyl sulfoxide, sulfolane, N-methylpyrrolidone, ethylene glycol dialkyl ethers, di-, tri- or tetra-ethylene glycol dialkyl ethers, in particular dimethyl or diethyl ether, toluene, xylene, chlorobenzene or liquid sulfur dioxide, or mixtures of two or more of the said solvents. It can also be particularly advantageous to carry out the first component stage of the process, i.e. reactions of II, III and IV, or of II and IV, in a polar aprotic organic or inorganic solvent, for example, such as acetonitrile or liquid sulfur dioxide, and to carry out the following stage(s) in less polar aprotic organic solvents, for example, such as toluene or xylene.

In those cases where compounds of the formula II and/or the formula III are not completely soluble in the chosen solvent, the reaction can be speeded up by very thorough mixing of the reactants, for example by means of vigorous stirring or by sonication.

In reacting the compounds of the formulae II, III and IV, the compounds of the formulae III and IV can, for example, be reacted first, for example at a reaction temperature of 0° to 80° C. without solvent or in the presence of one of the said aprotic polar organic or aprotic polar inorganic solvents, resulting in the formation of an addition compound of indeterminate structure (adduct 1). After that the reaction of II with the previously obtained adduct 1, most simply in the form of the previously obtained reaction mixture, is carried out, where appropriate with heating, resulting once again in the formation of an addition compound of indeterminate structure (adduct 2), which is suitable for the reaction according to the invention with the compound of the formula V. The reaction with the compound II is effected, for example, at a reaction temperature of 0° to 200° C., preferably of +8° C. to +135° C., in particular of +20° C. to +90° C. in the presence of one of the said aprotic polar organic or aprotic polar inorganic solvents. It is frequently advantageous to carry out the said reactions of the compounds II, III and IV using an ascending temperature gradient rather than at constant temperature.

According to results of investigations with detection reactions and spectroscopic methods, the addition compounds arising as intermediates do not, as initially thought, comprise an isocyanate of the formula $R^1XSO_2$—$N$=$C$=$O$, although, when viewed formally, the reaction of adduct 2 with the amine of the formula V to yield the substituted urea of the formula I at least gives the same result as would be expected from the reaction of an isocyanate of the formula $R^1XSO_2NCO$ with the amine of the formula V.

The invention therefore also relates to the said adducts 1 and 2 which can be obtained by the said variants of the reactions of compounds III and IV and of the subsequent reaction with compound II according to the process according to the invention.

In an alternative embodiment, the compounds of the formulae II, III and IV can be introduced together, preferably at a low temperature down to −10° C. or less, and heated together to the reaction temperature. In a further variant of the process the compounds of the formulae II and III can be introduced together and the sulfuryl chloride (compound of the formula IV) can be added either before heating to the reaction temperature or at the reaction temperature of the reaction of the compound of the formula II.

The reaction of the compounds of the formulae II, III and IV is preferably carried out under aprotic conditions.

In those cases where $R^7$ or $R^8$, or both, are hydrogen, it is, as a rule, expedient to employ one mole equivalent of an auxiliary base for each mole equivalent of hydrogen. Inorganic bases such as, for example, alkaline earth metal carbonates and/or bicarbonates, alkali metal carbonates and/or bicarbonates, and similar bases, or organic bases, such as, for example, trialkylamines, may be used as auxiliary bases.

In the case where $R^7$ is=hydrogen, it is as, as a rule, advantageous to employ the compounds of the formulae II and III, in which $R^8$ is not identical to hydrogen, in the molar ratio II:III of at most about 1:2, in particular in the molar ratio of about 1:2, with at least one mole equivalent of the compound III serving as the auxiliary base. If a molar ratio II:III of about 1:1 is also used in the case where $R^7$ is=hydrogen, it is advantageous for complete reaction to employ at least about one equivalent of another auxiliary base or, if, in addition, $R^8$ is=-hydrogen, at least two equivalents of another auxiliary base. The bases mentioned in the previous paragraph can be employed as the auxiliary bases.

In the case where $R^7$ and $R^8$ are each a metal cation or quaternary ammonium cation, the compounds II and III can also be employed without an auxiliary base, in the molar ratio of about 1:1.

Sulfuryl chloride (compound of the formula IV) is preferably equimolar to the compound of the formula II, or is employed in excess, for example in the molar ratio II:IV of 1:1 to 1:2, preferably 1:1 to 1:1.5. Larger excesses are also possible. It is, as a rule, expedient to remove by distillation sulfuryl chloride which has been added in excess before adding the compounds of the formula V.

The compounds of the formula V may be employed in an equimolar ratio to compounds of the formula II, or in less than equimolar or greater than equimolar ratio. Unreacted portions of V can be separated out of the reaction mixture by customary methods and reemployed for the process.

The starting compounds of the formulae III and IV required for preparing the compounds of the general formula I by the process according to the invention are available commercially or can be readily prepared by well known methods. The compounds of the formula II are either available commercially or can be prepared by analogy with customary methods, e.g. by means of reacting sulfochlorides with amines.

The heterocycles of the formula V are also either available commercially or can be readily prepared by suitable methods; see, e.g., US-A-4,310,470, EP-A-0027200, US-A-4,299,960, M. J. Langermann, C. K. Banks, J. Am. Chem. Soc. 73, 3011 (1951).

An advantage of the process according to the invention is that those portions of the compounds of the formulae IV and V which have not reacted, as well as the solvents which have been used, can be recovered virtually quantitatively and be reemployed in the process.

Secondary components which are not readily soluble, such as, for example, sodium chloride, may also be separated off between the reaction stages.

An additional advantage of the process according to the invention is that, as a rule, the desired products of the formula I, as compounds which are not readily soluble, precipitate out, where appropriate after the addition of water or other polar solvents, in high purity from the reaction medium.

In the following examples the percentage values relate to weight, unless otherwise indicated.

EXAMPLES

1.

1-[(N-Methylsulfonyl-N-methyl-amino)-sulfonyl]-3-(4,6-dimethoxy-2-pyrimidyl)-urea 340 g (2.52 mol) of sulfuryl chloride are introduced into 1.5 l of acetonitrile, and 260 g (4.0 mol) of sodium cyanate are added in portions within the space of 20 min while stirring vigorously (20° C.). The mixture is stirred for a further 15 min and then 222 g (2.0 mol) of N-methylmethanesulfonamide are added dropwise at 25° C., the temperature is raised slowly and the mixture is heated to reflux for 200 min while stirring vigorously. Subsequently, the excess sulfuryl chloride is distilled off with the solvent under 100 mbar up to an internal temperature of 50° C. After releasing the pressure under nitrogen, 1.5 l of acetonitrile (optionally also toluene etc.) are added and 155 g (1.0 mol) of 2-amino-4,6-dimethoxy-pyrimidine are introduced at 0° C. After 75 min, 1.0 l of water is added and the precipitate is separated off and washed. 304 g of 1-[(N-methylsulfonyl-N-methyl-amino)-sulfonyl]-3-(4,6-dimethoxy-2-pyrimidyl)-urea are obtained with a melting point of 176° to 178° C. The product is in accordance with a comparison sample and, according to analysis by high pressure liquid chromatography (HPLC), has a purity of 96%; yield: 77% of theory.

2.

1-(2-Ethoxyphenoxysulfonyl)-3-(4,6-dimethoxy-2-pyrimidyl)-urea 26.0 g (0.4 mol) of comminuted sodium cyanate are suspended at room temperature in 200 ml of acetonitrile, and 28.3 g (0.21 mol) of sulfuryl chloride are added within the space of 20 min, during which time the temperature rises to 44° C. After stirring for a further four hours at 50° C., the mixture is distilled under reduced pressure, cooled to 27° C. and 27.6 g (0.2 mol) of 2-ethoxyphenol are added within the space of 10 min. The mixture is left to stand overnight and 15.5 g (0.1 mol) of 2-amino-4,6-dimethoxypyrimidine are added at room temperature. The mixture is stirred at 50° C. for a further 120 min, the solvent is removed under reduced pressure, 100 ml of water are added, and the mixture is extracted with dichloromethane. After distilling off the organic solvent, 49.9 g of solids remain which, according to HPLC, exhibit a content of 71.6% by weight of 1-(2-ethoxyphenoxysulfonyl)-3-(4,6-dimethoxy-2-pyrimidyl)-urea. The yield of the compound is about 89% of theory.

The compounds of the formula I (Y=CH) listed in the following table are also obtained in analogy with the Examples 1 and 2.

| Example | $R^1$ | X | $R^3$ | $R^4$ | $R^5$ | $R^6$ | m.p.[°C.] |
|---|---|---|---|---|---|---|---|
| 3 | $CH_3$ | $SO_2N(C_3H_7)$ | $CH_3$ | $CH_3$ | H | H | 154–157 |
| 4 | $CH_3$ | $SO_2N[CH(CH_3)_2]$ | $CH_3$ | $CH_3$ | H | H | 120–122 |
| 5 | $C_2H_5$ | $SO_2N(C_2H_5)$ | $CH_3$ | $CH_3$ | H | H | |
| 6 | $CH_3$ | $SO_2N(CH_3)$ | $CH_3$ | $CH_3$ | H | H | |
| 7 | $CH_3$ | $SO_2N(CH_3)$ | $CH_3$ | $CH_3$ | H | $CH_3$ | |
| 8 | $C_4H_9$ | $SO_2N(CH_3)$ | $CH_3$ | $CH_3$ | H | H | |
| 9 | $CH_3$ | $SO_2N(cyclohexyl)$ | $CH_3$ | $CH_3$ | H | $CH_3$ | |
| 10 | $2\text{-}i\text{-}PrO\text{—}C_6H_4$ | O | $OCH_3$ | $CH_3$ | H | H | 141–143 | i-PrO = isopropoxy

I claim:

1. A process for preparing compounds of the formula I or salts thereof,

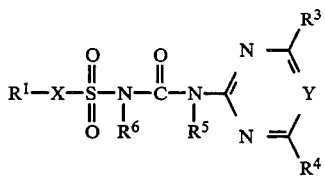

in which

X is oxygen, —O—$NR^2$— or —$SO_2$—NR2—,

Y is nitrogen or CH, $R^1$ is ($C_1$-$C_6$)alkyl, ($C_2$-$C_6$)alkenyl or ($C_2$-$C_6$)alkynyl, where each of the latter three radicals, independently of each other, is unsubstituted or substituted by one or more radicals selected from the group consisting of halogen, ($C_1$-$C_4$)alkoxy and [($C_1$-$C_4$)alkoxy]-carbonyl, or, in the case where X=oxygen, also phenyl, which is unsubstituted or substituted by one or more radicals selected from the group consisting of halogen, nitro, ($C_1$-$C_4$)alkyl, ($C_1$-$C_4$) haloalkyl, ($C_1$-$C_4$)alkoxy, ($C_1$-$C_4$) haloalkoxy and [($C_1$-$C_4$)-alkoxy]-carbonyl, $R^2$ is hydrogen, ($C_1$-$C_4$)alkyl, ($C_2$-$C_6$)alkenyl, ($C_2$-$C_6$)alkynyl or ($C_3$-$C_6$) cycloalkyl, $R^3$ and $R^4$, independently of each other, are hydrogen, ($C_1$-$C_4$)alkyl or ($C_1$-$C_4$)alkoxy, where each of the latter two radicals is unsubstituted or substituted by one or more radicals selected from the group consisting of halogen, alkoxy and alkylthio, or is halogen, ($C_1$-$C_4$)alkylthio, ($C_1$-$C_4$)alkylamino or di[($C_1$-$C_4$)alkyl]-amino and $R^5$ is hydrogen or ($C_1$-$C_4$)alkyl and $R^6$ is hydrogen wherein compounds of the formula II, $$R^1\text{—}X\text{—}R^7 \qquad (II)$$

in which $R^1$ and X are defined as in formula I and $R^7$ is hydrogen, a quaternary ammonium ion or one equivalent of a singly, double or multiply charged metal cation, are reacted in a one-pot process or in two or more stages with compounds of the formulae III, IV and V, $$R^8\text{—OCN} \qquad (III)$$

$$SO_2Cl_2 \qquad (IV)$$

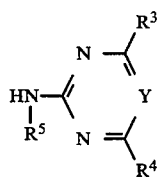

in which $R^3$, $R^4$, $R^5$, X and Y are defined as in formula I and $R^8$ is hydrogen, a quaternary ammonium ion or one equivalent of a singly, doubly or multiply charged metal cation, and wherein during the process, the compounds of formulae III and IV are reacted resulting in formation of an addition product (adduct 1).

2. The process as claimed in claim 1, wherein
$R^1$—X is N[($C_1$-$C_6$)-alkylsulfonyl]-N-[($C_1$-$C_3$)alkyl]-amino or [($C_1$-$C_4$)alkoxy]-phenoxy,
$R^3$ and $R^4$, independently of each other, are ($C_1$-$C_2$)alkyl or ($C_1$-$C_2$)alkoxy,
$R^5$ is hydrogen or methyl and
$R^6$ is hydrogen.

3. The process as claimed in claim 1, wherein $R^1$—X is N-[($C_1$-$C_3$)-alkylsulfonyl]-N-[($C_1$-$C_2$)-alkyl]-amino or ($C_1$-$C_3$)-alkoxyphenoxy.

4. The process as claimed in claim 1, wherein $R^3$ and $R^4$ are methyl or methoxy.

5. The process as claimed in claim 1, wherein the compounds of the formulae II, III and IV are first reacted with each other and the reaction with compounds of the formula V is carried out thereafter.

6. The process as claimed in claim 5, wherein the reaction temperature for the reactions of the compounds of the formulae II, III and IV is between 0° C. and 200° C.

7. The process as claimed in claim 5, wherein the reaction temperature for the reaction with the compound of the formula V is between −20° C. and 120° C.

8. The process as claimed in claim 1, wherein the process or individual stages of the process are carried out in the presence of inorganic or organic solvents which are inert under the reaction conditions, or in mixtures of these solvents.

9. The process as claimed in claim 8, wherein a solvent is employed selected from the group consisting of aprotic polar organic solvents and aliphatic and aromatic, where appropriate halogenated, hydrocarbons, and mixtures of the said organic solvents.

10. The process as claimed in claim 1, wherein the compounds of the formulae II, III and IV are reacted under aprotic conditions.

11. The process as claimed in claim 10, wherein
$R^8$ is a metal cation or a quaternary ammonium cation and the compounds of the formulae II and III are employed
 a) in the case where $R^7$=H, in a molar ratio of at most 1:2 or
 b) in the case where $R^7$=H, in a molar ratio of about 1:1 and in the presence of 1 mole equivalent of an auxiliary base which is different from compound III or
 c) in the case where $R^7$=metal cation or quaternary ammonium cation, in a molar ratio of about 1:1 without auxiliary base.

12. The process as claimed in claim 1, wherein the compound of the formula IV is equimolar to the compound of the formula II, or is employed in excess.

* * * * *